United States Patent
Hiskey et al.

(10) Patent No.: US 6,552,201 B2
(45) Date of Patent: Apr. 22, 2003

(54) PREPARATION OF 3,3'-DIAMINO-4,4'-AZOFURAZAN

(75) Inventors: Michael A. Hiskey, Los Alamos, NM (US); David E. Chavez, Ranchos de Taos, NM (US); Robert L. Bishop, Santa Fe, NM (US); John F. Kramer, Santa Fe, NM (US); Scott A. Kinkead, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 4 days.

(21) Appl. No.: 10/020,329

(22) Filed: Oct. 30, 2001

(65) Prior Publication Data

US 2002/0134476 A1 Sep. 26, 2002

Related U.S. Application Data

(62) Division of application No. 09/560,159, filed on Apr. 28, 2000, now Pat. No. 6,358,339.

(51) Int. Cl.[7] .............................................. C07D 271/08
(52) U.S. Cl. ......................................... 548/125; 149/36
(58) Field of Search ............................. 548/125; 149/36

(56) References Cited

U.S. PATENT DOCUMENTS

| | | | | |
|---|---|---|---|---|
| 3,711,609 A | * | 1/1973 | Lehmann et al. | 548/125 |
| 4,158,002 A | * | 6/1979 | Funahashi et al. | 534/566 |
| 4,353,758 A | * | 10/1982 | Akst et al. | 149/92 |
| 5,243,916 A | * | 9/1993 | Freche et al. | 102/481 |
| 5,460,669 A | * | 10/1995 | Willer et al. | 149/92 |
| 5,608,112 A | * | 3/1997 | Schwartz | 208/289 |
| 6,077,371 A | * | 6/2000 | Lundstrom et al. | 149/37 |
| 6,388,087 B1 | * | 5/2002 | Bashir-Hashemi et al. | 548/125 |

OTHER PUBLICATIONS

Solodyuk et al., [HCAPLUS AN 1981:480839], Zh. Org. Khim (1981), 17(4) 861–5.*
Sinditskii et al., [HCAPLUS AN 1998: 498929], Int. Annu. Conf. ICT (1998), 29th(Energetic materials), 170.1–170.11.*
Sheremetev et al., [HCAPLUS AN 1996:84537], J. Org. Chem. (1996), 61(4), 1510–11.*

* cited by examiner

*Primary Examiner*—Edward A. Miller
(74) *Attorney, Agent, or Firm*—Bruce H. Cottrell

(57) ABSTRACT

A method of preparing 3,3'-diamino-4,4'-azofurazan is provided together with a composition of matter including a mixture of 3,3'-diamino-4,4'-azofurazan and 1,3,5-triamino-2,4,6-trinitrobenzene.

1 Claim, No Drawings

PREPARATION OF 3,3'-DIAMINO-4,4'-AZOFURAZAN

This application is a divisional of Ser. No. 09/560,159 filed on Apr. 28, 2000 by Hiskey et al. now U.S. Pat. No. 6,358,339.

FIELD OF THE INVENTION

The present invention relates to derivatives of 3,4-diaminofurazan useful as insensitive high explosive materials. This invention was made with government support under a contract with the Department of Energy (Contract No. W-7405-ENG-36).

BACKGROUND OF THE INVENTION

The synthesis of 3,4-diaminofurazan was first reported by Coburn in J. Heterocyclic Chem., vol. 5, pp. 83–87 (1968). Since then a large body of work has been accumulated on the oxidation of 3,4-diaminofurazan, especially by Russian scientists, e.g., Solodyuk et al., in Zh. Org. Khim., vol. 17(4), pp. 756–759 (1981) wherein the compounds 3,3'-diamino-4,4'-azoxyfurazan (DAAF) and 3,3'-diamino-4,4'-azofurazan (DAAzF) were described. They used a variety of peroxide reagents on 3,4-diaminofurazan to prepare 3,3'-diamino-4,4'-azoxyfurazan (DAAF), 3,3'-diamino-4,4'-azofurazan (DAAzF) and 3-amino-4-nitrofurazan usually as mixtures which were separated by differing solubilities. However, no characterization of the explosive properties of these compounds was reported.

One previously known explosive formulation included a combination of 2,2',4,4',6,6'-hexanitrostilbene (HNS) and 1,3,5-triamino-2,4,6-trinitrobenzene (TATB). While this formulation has been useful, it suffers some drawbacks in terms of performance and safety. Improved formulations including TATB have been sought.

The present inventors undertook a study of the compounds 3,3'-diamino-4,4'-azoxyfurazan (DAAF) and 3,3'-diamino-4,4'-azofurazan (DAAzF). Through their efforts, it was found that the compounds 3,3'-diamino-4,4'-azoxyfurazan (DAAF) and 3,3'-diamino-4,4'-azofurazan (DAAzF) were both useful as insensitive high explosive materials. In addition, an improved synthesis of 3,3'-diamino-4,4'-azofurazan (DAAzF) was developed. Also, formulations of 3,3'-diamino-4,4'-azofurazan (DAAzF) and 1,3,5-triamino-2,4,6-trinitrobenzene (TATB) should overcome the drawbacks of TATB/HNS formulations.

It is an object of this invention to provide an improved process for preparation of 3,3'-diamino-4,4'-azofurazan (DAAzF).

Another object of the present invention is to provide for use of 3,3'-diamino-4,4'-azoxyfurazan (DAAF) and 3,3'-diamino-4,4'-azofurazan (DAAzF) as insensitive high explosive materials.

Still another object of the present invention is to provide formulations including 1,3,5-triamino-2,4,6-trinitrobenzene (TATB) and 3,3'-diamino-4,4'-azofurazan (DAAzF).

SUMMARY OF THE INVENTION

To achieve the foregoing and other objects, and in accordance with the purposes of the present invention, as embodied and broadly described herein, the present invention provides for the use of 3,3'-diamino-4,4'-azoxyfurazan (DAAF) and 3,3'-diamino-4,4'-azofurazan (DAAzF) as insensitive, high explosive materials.

The present invention further provides a process for the preparation of 3,3'-diamino-4,4'-azofurazan (DAAzF) from 3,4-diaminofurazan.

The present invention further provides a composition including 3,3'-diamino-4,4'-azofurazan and 1,3,5-triamino-2,4,6-trinitrobenzene (TATB).

DETAILED DESCRIPTION

The present invention is concerned with insensitive, high explosive materials. The particular insensitive, high explosive materials of the present invention include 3,3'-diamino-4,4'-azoxyfurazan (DAAF) and 3,3'-diamino-4,4'-azofurazan (DAAzF). Neither compound has previously been known as insensitive, high explosive material.

In addition to the use of these particular compounds as insensitive, high explosive materials, the present invention is concerned with compositions including 3,3'-diamino-4,4'-azofurazan and 1,3,5-triamino-2,4,6-trinitrobenzene (TATB).

By the term "insensitive", it is generally meant that the material has a drop height of greater than 320 cm as measured by using a 2.5 kg falling weight (Type 12).

Both 3,3'-diamino-4,4'-azoxyfurazan (DAAF) and 3,3'-diamino-4,4'-azofurazan (DAAzF) derive a significant amount of their energy of detonation from their intrinsically high heats of formation ($\Delta H_f$) and not from oxidation of carbon in the backbone. This, in a large part, is due to the presence of the azo- and azoxy-linkage. As an example of this, 3,3'-diamino-4,4'-azofurazan only has enough available oxygen to burn its hydrogen to water and none to oxidize carbon, yet it has better explosive performance than HNS (2,2',4,4',6,6'-hexanitrostilbene) which is able to burn 64% of its carbon to CO. In addition, the impact sensitivity of 3,3'-diamino-4,4'-azofurazan was determined to be greater than 320 cm while the drop height of HNS was published (Dobratz, "Lawrence Livermore National Laboratory Explosives Handbook. Properties of Chemical Explosives and Explosives Simulants", National Technical Information Service, UCRL-52997, 1981) to be 54 cm (2.5 kg, Type 12).

Pure 3,3'-diamino-4,4'-azoxyfurazan (DAAF) is an orange-yellow crystalline powder having a DSC onset of 248° C. and an x-ray crystal density of 1.747 g/cm$^3$. DAAF was found to have a drop height of greater than 320 cm (2.5 Kg, Type 12) and elicited no response to spark (>0.36 J) or friction (>36 kg, BAM). DAAF had a measured $\Delta H_f$=+106 kcal/mole. Low density pellets of DAAF could be pressed neat but high density pellets tended to wafer and therefore required formulation with 5 volume percent of latex Kel-F 800 resin (a chlorotrifluoroethylene/vinylidene fluoride copolymer, available from 3M Company). This allowed pressing of pieces up to a density of 1.70 g/cm$^3$ (97% of theoretical maximum density). A Henkin critical temperature was determined to be 241° C. for the Kel-F formulated material and 252° C. for the neat material.

The explosive performance properties of DAAF were examined. A poly-ρ test, which determines detonation velocity as a function of density, was performed at two diameters, 0.5 in. and 0.25 in. These two diameters revealed that the detonation velocity was relatively independent of diameter. The detonation velocity of DAF was determined to be 8.0 kilometers per second (km/s) at a density of 1.69 g/cm$^3$. This data was further verified by an unconfined rate stick of pellets at a density of 1.69 g/cm$^3$ and 3 mm in diameter. As evidenced by the witness plate a complete detonation was achieved. Unfortunately, this test was too small to be instrumented accurately to determine detonation velocity. A failure diameter of less than 3 millimeters (mm) is unprecedented in a material which is insensitive to impact. The detonation pressure ($P_{CJ}$) was estimated to be 299 kbar from a 0.5-inch diameter plate dent at a density of 1.69 g/cm$^3$.

Shock sensitivity was characterized by performing six wedge tests, in which the DAAF was plastic-bonded with 5% Kel-F 800 resin and pressed to 1.705 g/cm$^3$. There have been many variations on the wedge test; the present one is the so-called "mini-wedge" test (see Seitz, Shock Waves in Condensed Matter, 531 (1983) and Hill et al., Shock Compression of Condensed Matter, 803 (1995)) which is designed to use a minimal amount (about 7 g) of sample explosive. Material conservation is desirable for screening new explosives, due to cost.

From the wedge testing, it was found that DAAF was quite like HMX so far as shock sensitivity was concerned.

The explosive energy was characterized by performing a standard 1-inch cylinder test on DAAF neat-pressed to 1.691 g/cm$^3$. The cylinder energy was determined to be 1.22 kilojoules per gram (kJ/g) for DAAF. The test consists of a 1.00-inch inner diameter, 0.10-inch wall copper tube filled with explosive and detonated at one end. The pressure of the explosive products expands the tube in a funnel shape. With proper care the tube will typically expand to about three times its initial diameter before it begins to fragment. To achieve this much expansion requires very tight mechanical tolerances and high standards of purity, temper, and grain size for the copper. These requirements are laid out in more detail by Hill et al., Los Alamos Report LA-13442-MS (1998), such report incorporated herein by reference.

The detonation velocity was also measured via ten pin switches, each consisting of 2-mil diameter enameled copper wire. When the detonation passed a wire, the insulation was promptly destroyed and the wire shorted to the tube. This fired an R-C circuit that was observed on an oscilloscope. The resulting detonation velocity was 8.020 mm/$\mu$/s. The random error, i.e., the standard error in velocity associated with the linear fit to the x-t data, was 2.7 m/s.

Although the azo-compound DAAzF has less available oxygen than DAAF, it has a higher measured $\Delta H_f$ (+128 kcal/mol). Also, the detonation velocity of DAAzF was determined to be 7.6 km/s at a density of 1.65 g/cm$^3$ in the poly-$\rho$ test. The thermal stability of DAAzF was also attractive having a DSC onset of 315° C., which is comparable to that of HNS. The previous procedure for preparing DAAzF only yielded inseparable mixtures as did the reduction of DAAF with triphenylphosphine; therefore a new method of synthesizing DAAzF from readily available DAAF was developed. The process involved formation of a hydrazine intermediate from DAAF by reduction with acetic acid and zinc followed by the oxidation to DAAzF by bubbling air through a methanol solution.

The DAAzF, a dark-orange crystalline solid, was found insensitive to impact ($H_{50}$>320 cm, Type 12), spark (>0.36 J) and friction (>36 kg, BAM). The explosive performance of DAAzF was lower in both velocity and pressure as the increase in heat of formation was not sufficient to offset the drop in oxygen balance compared to the DAAF. The DAAzF was formulated with 5 volume percent latex Kel-F 800 and the detonation velocity as a function of density was determined at two different diameters, 0.5 inches and 0.25 inches. The velocity was more dependent on diameter than with DAAF. Despite this dependence a 3 mm diameter shot at a density of 1.65 g/cm$^3$ detonated cleanly with no confinement. A 0.5-inch diameter plate dent allowed the calculation of a detonation pressure to be 262 kbar at a density of 1.65 g/cm$^3$.

The present invention is more particularly described in the following examples which are intended as illustrative only, since numerous modifications and variations will be apparent to those skilled in the art.

All starting materials were obtained from commercial sources or prepared from the referenced literature. All NMR spectra were obtained on a JEOL GSX-270 spectrometer, and chemical shifts are reported relative to internal tetramethylsilane. Melting points were determined at 2° C./min with a Mettler FP1 apparatus and are corrected or by Differential Scanning Calorimetry (DSC) at 2° C./min. IR spectra were obtained on a Bio-Rad FTS40 FTIR spectrometer.

EXAMPLE 1

3,3'-Diamino-4,4'-azoxyfurazan (DAAF)

This procedure was modeled from the original Russian preparation. To 30% hydrogen peroxide (100.0 g, 0.88 mol) in a 500 ml jacketed flask maintained at 18° C. was added 98% sulfuric acid (55.0 g, 0.56 mol) over 10 minutes with stirring. Then, 3,4-diaminofurazan (10.0 g, 0.10 mole) was added. The suspension was stirred for 24 hours in which time the soluble green nitroso-amino-furazan was converted to the insoluble orange DAAF. The product was filtered on a glass frit, washed with water and air dried to yield 9.29 g (88%) of crude material. For recrystallization the crude compound was dissolved in the minimum amount of room temperature DMSO (approximately 22 ml) and then water (45 ml) was added over 5 minutes with stirring. The pure DAAF was filtered, washed with water and air-dried. This material had the same properties as previously reported by the Russians. $^1$H NMR (deuteriomethylsulfoxide)$\delta$ 6.65 (s, 2H), 6.93 (s, 2H); $^{13}$C NMR (deuteriomethylsulfoxide) $\delta$ 148.3, 151.2, 152.6, 153.9.

EXAMPLE 2

3,3'-Diamino-4,4'-hydrazofurazan

A 1 liter Erlenmeyer flask was charged with 200 ml of methanol, crude DAAF (10.6 g, 0.050 mol) and zinc dust (9.77 g, 0.150 mol). To this suspension was added glacial acetic acid (9.0 g, 0.150 mol) dropwise over 10 minutes with good stirring. The slurry was stirred for 1 hour and then filtered through a bed of Celite. The bed was washed with methanol and the solvent removed under reduced pressure to yield 9.90 g (100%). An analytical sample was recrystallized from water to give a monohydrate, mp 192° C. (dec.); $^1$H NMR (deuteriomethylsulfoxide)$\delta$ 5.90 (s, 4H), 8.43 (s, 2H); $^{13}$C NMR (deuteriomethylsulfoxide)$\delta$ 148.6 150.3; IR (KBr) 3399, 3328, 3220, 3042, 1648, 1577, 1555, 1439, 1293, 913, 816 cm$^{-1}$.

Anal. Calcd for $C_4H_6N_8O_2H_2O$: C, 22.23; H, 3.73; N, 51.87. Found C, 22.03; H, 3.82; N, 52.27.

EXAMPLE 3

3,3'-Diamino-4,4'-azofurazan (DAAzF)

Air was bubbled through the methanol solution of the hydrazo-furazan of Example 2, prepared as above, for 20 hours with stirring at room temperature. The orange precipitate was filtered, washed with methanol and air dried to yield 9.0 g (92%) of pure 3,3'-diamino-4,4'-azofurazan with the same properties as previously reported by the Russians. $^1$H NMR (deuteriomethylsulfoxide)$\delta$6.89 (s, 4H); $^{13}$C NMR (deuteriomethylsulfoxide) $\delta$ 150.4, 155.6.

EXAMPLE 4

A mixture of 50 percent by weight DAAzF and 50 percent by weight TATB is formed and is tested for detonation velocity as a function of density, at two diameters, 0.5 inches and 0.25 inches. The performance is anticipated as better than that obtainable from a mixture of 50 percent by weight HNS and 50 percent by weight TATB. Variations in weight percentages are equally suitable.

Although the present invention has been described with reference to specific details, it is not intended that such details should be regarded as limitations upon the scope of the invention, except as and to the extent that they are included in the accompanying claims.

What is claimed is:

1. A method of preparing 3,3'-diamino-4,4'-azofurazan comprising:

reacting 3,3'-diamino-4,4'-azoxyfurazan with acetic acid in the presence of zinc metal to form 3,3'-diamino-4,4'-hydrazofurazan; and, oxidizing said 3,3'-diamino-4,4'-hydrazofurazan to 3,3'-diamino-4,4'-azofurazan.

* * * * *